United States Patent [19]

Goggin et al.

[11] Patent Number: 5,563,259

[45] Date of Patent: Oct. 8, 1996

[54] PROCESS FOR MAKING β-O-CELLOBIOSYL STEROID DERIVATIVES AND TRIMETHYL SILYL STEROID INTERMEDIATES USED THEREIN

[75] Inventors: Kathleen D. Goggin, Colchester; John F. Lambert, North Stonington; Stanley W. Walinsky, Mystic, all of Conn.

[73] Assignee: Pfizer Inc., New York, N.Y.

[21] Appl. No.: 351,471

[22] PCT Filed: Mar. 2, 1993

[86] PCT No.: PCT/US93/01709

§ 371 Date: Dec. 20, 1994

§ 102(e) Date: Dec. 20, 1994

[87] PCT Pub. No.: WO94/00478

PCT Pub. Date: Jan. 6, 1994

Related U.S. Application Data

[63] Continuation of Ser. No. 905,595, Jun. 26, 1992, abandoned.

[51] Int. Cl.$^6$ .............. C07G 17/00; C07J 71/00
[52] U.S. Cl. .................. 536/124; 536/123.130; 540/17; 540/19; 540/20
[58] Field of Search ............... 536/123.13, 124; 540/17, 19, 20

[56] References Cited

U.S. PATENT DOCUMENTS

| | | | |
|---|---|---|---|
| 2,991,282 | 4/1961 | Rubin | 540/18 |
| 3,303,187 | 2/1967 | Rubin | 540/18 |
| 3,935,194 | 1/1976 | Loken | 540/18 |
| 4,260,603 | 4/1981 | Pegel et al. | 514/26 |
| 4,602,003 | 7/1986 | Malinow | 514/26 |
| 4,602,005 | 7/1986 | Malinow | 514/26 |
| 5,010,185 | 4/1991 | Urban | 536/6.1 |

FOREIGN PATENT DOCUMENTS

| | | |
|---|---|---|
| 0159431 | 10/1985 | European Pat. Off. . |
| 0403150 | 12/1990 | European Pat. Off. . |
| 3264595 | 11/1991 | Japan . |
| 2024624 | 1/1980 | United Kingdom . |
| 9311150 | 6/1993 | WIPO . |
| 9400480 | 1/1994 | WIPO . |
| 9400479 | 1/1994 | WIPO . |

OTHER PUBLICATIONS

Caglioti et al., "The Reaction of Tosylhydrazones with Lithium Hydride," *Tetrahedron*, 19, 1127–1131 (1963).

Freudenberg et al., "Synthese der Methylierten Cellotriose (Dekamethyl–β–methylcellotriosid)," *J. Liebig Ann. Chem.*, 494, 63–68 (1932).

Malinow et al., "Effects of α–and β–Tigogenin Cellobiosides on Cholesterol Absorption," *Steroids*, 48 (3–4), 197–211 (1986).

Marker et al., "Steroidal Sapogenins," *J. Am. Chem. Soc.*, 69, 2167–2211 (1947).

Schmidt, "New Methods for the Synthesis of Glycosides and Oligosaccharides—Are There Alternatives to the Koenigs–Knorr Method?" *Angew. Chem. Intl. Ed. Eng.*, 25, 212–223 (1986).

McCarthy, "Synthesis of [5,6–$^3$H$_2$]CP–88,818 (β[5,6–$^3$H$_2$] Tigogenin Cellobioside)," *J. Labelled Compounds and Radiopharmaceuticals*, 28(10), 1150–1159 (1990).

Noyori et al., "Glycosidation of Alcohol and Sugar Derivatives," *Chem. Abstr.*, 104, Abstr. No. 168,762q (1986); Abstr. of JP 60, 159,699 [85,159,699], publ. Aug. 16, 1985; only Abstract supplied.

Urban et al., Synthesis of Tigogen (β–O–Cellobioside Heptacetate and Glycoside Tetraacetate via Schmidt's Trichloroacetimidate Method, Some New Observations, *Tetrahedron Letters*, vol. 31, pp. 4421–4424 (1990).

Hashimoto et al., Glycosylation Using Glucopyranosyl Fluorides and Silicon–Based Catalysts, *Tetrahedron Letters*, vol. 25, No. 13, pp. 1379–1382 (1984).

Nishizawa et al., Total Synthesis of Cyclo–L–Cyclo–L–Rhamnohexase by a Stereoselective Thermal Glycosylation, *Tetrahedron Letters*, vol. 32, No. 40, 5551, (1991).

R. Mietchen et al., Reactions with and in Anhydrous Hydrogen Fluoride[1]. Selective Systems of Glycosyl Flourides. Z. Chem. vol. 30, 2, pp. 56–67 (1990) (Translation provided).

Nishizawa et al., Thermal Glycosidation with Benzylated Glycosyl Chlorides: A Very Simple Procedure for O–Glycosidation, Chem. Pharm. Bull., 37 (2), 565 (1989).

J. E. Oliver et al., "Glucosylations of Pregn–5–ene–3–beta,20R–diol", Steroids: Structure, Function, and Regulation, 52, 3, pp. 265–278 (1988).

H. Kunz et al., "Stereoselective Glycosylation of Alcohols and Silyl Ethers Using Glycosyl Fluorides and Boron Trifluoride Etherate", Helvetica Chimica Acta, 68, 1, pp. 283–287, (1985).

*Primary Examiner*—John Kight
*Assistant Examiner*—L. Eric Crane
*Attorney, Agent, or Firm*—Peter C. Richardson; Gregg C. Benson; A. Dean Olson

[57] ABSTRACT

A process for the synthesis of peracyl-1-O-steroidal-β-cellobiosides that provides excellent β-anomeric selectivity without the use of a metal salt promoter. The process comprises reacting heptaacyl-β-D-cellobiosyl-1-fluoride and a trisubstituted silyl-3-O-steroid, wherein the steroid is tigogenin, hecogenin, 11-ketotigogenin or diosgenin in the absence of a metal salt under suitable conditions.

11 Claims, No Drawings

PROCESS FOR MAKING β-O-CELLOBIOSYL STEROID DERIVATIVES AND TRIMETHYL SILYL STEROID INTERMEDIATES USED THEREIN

This application was filed under 35 U.S.C. §371 based on PCT/US93/01709, which was filed on Feb. 3, 1993 which is a continuation of U.S. application Ser. No. 07/905,595 which was filed on Jun. 26, 1992 and is now abandoned.

BACKGROUND OF THE INVENTION

The present invention relates to a process for the synthesis of steroidal glycosides, and particularly to the preparation of diosgenyl, tigogenyl, 11-ketotigogenyl and hecogenyl β-O-cellobioside heptaalkanoates used as intermediates therein.

Tigogenin beta-O-cellobioside is a known compound having utility in the treatment of hypercholesterolemia and atherosclerosis (Malinow, U.S. Pat. Nos. 4,602,003 and 4,602,005; Malinow et al., Steroids, vol. 48, pp. 197–211, 1986). Each patent discloses a different synthesis of this compound from alpha-D-cellobiose octaacetate; the first via the glycosyl bromide heptaacetate which is coupled with tigogenin in the presence of silver carbonate, and finally hydrolyzed; and the second via direct stannic chloride catalyzed coupling of the cellobiose octaacetate with tigogenin in methylene chloride, again followed by hydrolysis. In Malinow et al., reaction of cellobiose octaacetate with titanium tetrabromide gave the cellobiosyl bromide heptaacetate, which was coupled with tigogenin by means of mercuric cyanide, and then hydrolyzed. All of these methods have serious drawbacks for producing bulk material to be used as a pharmaceutical drug. A desirable goal, met by the present invention, has been to devise synthetic methods which avoid toxic metal salts and/or expensive reagents, and which cleanly produce the desired tigogenin beta-O-cellobioside, avoiding tedious and expensive purification steps.

Schmidt, Angew. Chem. Int. Ed. Engl., vol. 25, pp. 212–235 (1986) has reviewed the synthesis and reactions of O-glycosyl trichloroacetimidates formed by the reaction of sugars possessing a 1-hydroxy group (but with other hydroxy groups protected, e.g., by benzyl or acetyl) with trichloroacetonitrile in the presence of a base. There is preferential formation of the alpha-anomer when sodium hydride is used as base, and preferential formation of the beta-anomer when the base is potassium carbonate. The alpha anomer of tetrabenzylglucosyl trichloroacetimidate when coupled with cholesterol gave anomeric mixtures which varied with catalyst (p-toluenesulfonic acid or boron trifluoride etherate) and temperature (−40° to +20° C.). On the other hand, both the alpha and beta anomers of tetraacetylglucosyl trichloroacetimidate analog reportedly yield exclusively beta-anomeric products.

Thus, there has been a continuing search in this field of art for improved methods of stereocontrolled syntheses of steroidal glycosides.

SUMMARY OF THE INVENTION

This invention is directed to a process for the synthesis of peracyl-1-O-steroidal-β-cellobiosides that provides excellent β-anomeric selectivity without the use of a metal salt promoter. The process comprises reacting heptaacyl-β-D-cellobiosyl-1-fluoride and a trisubstituted silyl-3-O-steroid, wherein the steroid is tigogenin, hecogenin, 11-ketotigogenin or diosgenin in the absence of a metal salt under suitable conditions. Typically the acyl is alkanoyl($C_1$–$C_6$), benzoyl or toluoyl and the silyl substitution is alkyl($C_1$–$C_6$), phenyl or phenyl alkyl($C_1$–$C_6$). In a particularly efficient, preferable process, the glycosyl compounds and steroids are reacted neat.

Another aspect of this invention are the compounds trimethylsilyl-3-O-hecogenin, trimethylsilyl-11-keto-3-O-tigogenin and trimethylsilyl-3-O-tigogenin. These compounds are useful intermediates to the above steroidal glycosides.

Other features and advantages will be apparent from the specification and claims.

DETAILED DESCRIPTION OF THE INVENTION

Preferably the peracyl-D-saccharidyl-1-halide used to couple with the steroid is heptaacyl-D-cellobiosyl-1-halide. As used herein the term peracyl refers to the substitution by an acyl group on each of the available hydroxy positions of the saccharidyl moiety. Preferably, the peracyl-D-saccharidyl-1-halides are the beta anomer. In addition, it is preferred that the halide is fluoride. It is also preferred that the acyl is alkanoyl($C_1$–$C_6$), benzoyl or toluoyl and especially preferred that the acyl is acetyl. The compounds may be prepared from conventional starting materials according to methods described in K. Freudenberg and W. Nagai, Ann., 494,63 (1932) and in R. Miethchen, G. Kolp, D. Peters, and J. Holz, Z. Chem. 30, 56 (1990). It is preferred that about 0.5 equivalents (as used herein equivalents is based on the steroidal silyl ether) to about 1.5 equivalents peracyl-D-cellobiosyl-1-fluoride be used. It is especially preferred that a substantially stoichiometric quantity of peracyl-β-D-cellobiosyl-1-fluoride be used as this avoids using excess reagents while maintaining excellent stereospecificity.

Any reaction inert solvent may be used. As used above and elsewhere herein, the expression "reaction-inert solvent" refers to a solvent which does not react or decompose with starting materials, reagents, intermediates or products in a manner which adversely affects the yield of the desired product. In general, the solvent can comprise a single entity, or contain multiple components. Although the solvent can be an aromatic or alkane hydrocarbon solvent (e.g. alkyl ($C_1$–$C_6$; branched or unbranched) benzene, dialkyl ($C_1$–$C_6$) benzene, trialkyl ($C_1$–$C_6$) biphenyl, alkane ($C_4$–$C_{20}$; branched or unbranched), cycloalkane ($C_5$–$C_8$), bicycloalkane) it is especially preferred that the reaction be performed neat.

Tigogenin's preparation is described by Rubin in U.S. Pat. Nos. 2,991,282 and 3,303,187, by B. Löken in U.S. Pat. No. 3,935,194 and Caglioti et al., Tetrahedron 19, 1127 (1963). It is a natural product which can be isolated from plants. Its structure is depicted below.

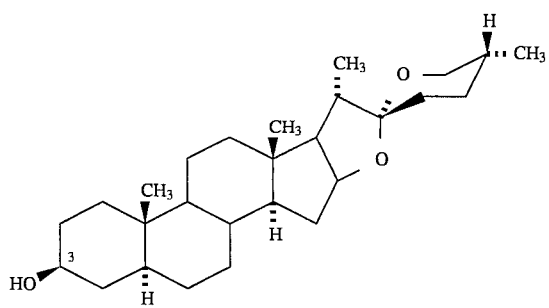

Hecogenin's preparation is described in a paper on Steroidal Sapogenins by Russell E. Marker et al., in J. Amer. Chem. Soc., 69, 2167–2211 (1947). It is a natural product which can be isolated from plants. Its structure is depicted below.

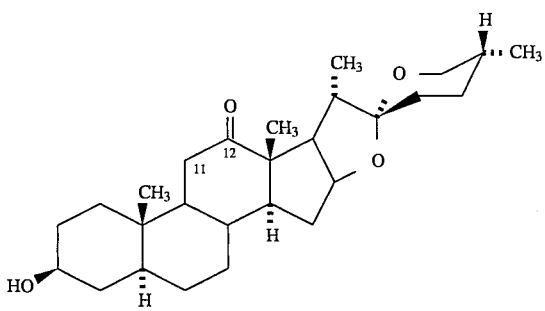

11-ketotigogenin switches the carbonyl group from the 12 position of the hecogenin structure to the 11 position. 11-Ketotigogenin is prepared from hecogenin by the following procedure. According to the procedure of Conforth, et al., (J. Chem. Soc., 1954, 907), hecogenin is acetylated, brominated, treated with sodium hydroxide and reduced with zinc to give the 12-hydroxy-11-keto analog. The 12-hydroxy-11-keto analog is then acetylated and reduced with calcium and ammonia to give 11-ketotigogenin.

Diosgenin's preparation is described in "Diosgenin and other Steroidal Drug Precursors" by Asolkar, L. V., Chadha, Y. R., and Rawat, P. S., Council of Scientific and Industrial Research, New Delhi, India, 183 pages, 1979 and also in T. Kawasaki et al., Chem. Pharm. Bull., Japan 10, 698 (1962). It is a natural product which can be isolated from plants. Its structure is depicted below.

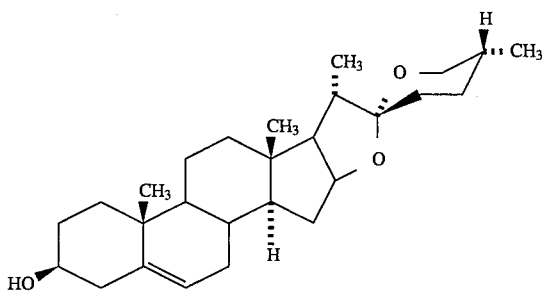

Although any trisubstituted silyl ether (3-hydroxy substitution) of the above steroids may be coupled with the peracyl saccharidyl halides it is preferred that an alkyl ($C_1$–$C_6$) or aryl (i.e. phenyl, alkyl($C_1$–$C_6$)phenyl) trisubstituted silyl ether be used. It is especially preferred that a trialkyl ($C_1$–$C_6$) silyl ether be used, particularly trimethyl silyl ether, t-butyldimethyl silyl ether, triisopropyl silyl ether, phenyldimethyl silyl ether or triethyl silyl ether.

The above silyl ether steroids may be prepared by reacting a trisubstituted silyl trifluoromethanesulfonate with the appropriate steroid in the presence of a trialkylamine (e.g. triethylamine) at a temperature less than about 10° C. for about 0.5 to about 6 hours. Appropriate procedures may also be found in L. Birkofer and A. Ritter, "Newer Methods in Preparative Organic Chemistry," Vol. V. p. 211, Academic Press, New York, N.Y. 1968 or A. E. Pierce, "Silylation of Organic Compounds," Pierce Chemical Co., Rockford, Ill., 1968, or J. F. Klebe, Acc, Chem. Res., 1970 (3) 299.

Preferably about 0.5 equivalent (as used herein equivalents is based on the glycosyl halide) to about 1.5 equivalents of the silylated steroid is used. It is especially preferred that a substantially stoichiometric quantity of the steroidal silyl ether be used as this avoids using excess reagents.

Any environment or conditions (e.g., pressure, temperature, time, solvent,) suitable for (i.e., capable of) forming the desired 1-O-steroidal peracyl-β-cellobiosides may be used. However, it is preferred that the reaction occurs at a temperature of about 100° C. to about 220° C. and preferably from about 150° C. to about 195° C. Below about 100° C. the reaction can be slow and above about 240° C. undesired side reactions (e.g. decomposition) can occur. This reaction is conveniently carried out at ambient pressure however, pressures from about 0.5 to about 3 atmospheres may be used.

Preferably the silylated steroid, β-cellobiosyl fluoride heptaacetate, and optional solvent are combined and heated for about 0.5 to about 6.0 hours, typically under nitrogen. The desired compounds are then isolated by conventional methods.

Although the above process is designed to synthesize steroidal glycosides of the βconfiguration, the more thermodynamically stable β-anomers are accessible by acid-catalyzed isomerization of the β-glycosides. Therefore, for example, tigogenyl α-O-cellobioside heptaalkanoate can be prepared from tigogenyl β-O-cellobioside heptaalkanoate by heating the β-glycoside in a methylene chloride solution containing hydrogen bromide.

This invention makes a significant advance in the filed of steroidal glycosides by providing an efficient method of preparing diosgenin-, tigogenin-, hecogenin or peracyl-11-ketotigogenin-β-O-cellobiosides which are useful intermediates to the deacylated end products. The deacylated end products are useful antihypercholesterol agents. The process provides high productivity, excellent β-anomeric selectivity, reduced reaction by-products (e.g. inorganic salts) without the need for a metal salt activator.

It should be understood that the invention is not limited to the particular embodiments shown and described herein, but that various changes and modifications may be made without departing from the spirit and scope of this novel concept as defined by the following claims and examples.

EXAMPLE 1

Reaction of β-Cellobiosyl Fluoride Heptaacetate with Trimethylsilyl-O-Tigogenin

β-Cellobiosyl fluoride heptaacetate (10.45 g; 15.1 mmol) and trimethylsilyl-O-tigogenin (8.00 g; 16.4 mmol) were combined in 56 ml of o-xylene under nitrogen. The white slurry was heated to 140° C. and then maintained at 140°–145° C. for 6 hours. Thin-layer chromatography (ethyl acetate/hexanes 1:1) showed only a trace of residual acetofluoro-β-D-cellobiose so the reaction was cooled to room temperatures. Analysis of the reaction mixture by high-pressure liquid chromatography showed that tigogenyl β-O-cellobioside heptaacetate was formed in 40.0% yield. Tigogenyl α-O-cellobioside heptaacetate was present in approximately 0.4% yield.

Additional β-glycosides which were prepared from the corresponding trimethylsilyl ethers are reported in Table 1 (below).

TABLE 1

Thermal Reactions of Trimethylsilyl Ethers with β-Cellobiosyl Fluoride Heptaacetate

| REACTIONS | | | | YIELD | |
|---|---|---|---|---|---|
| TMS Ether | Time | Temp | Solvent | β-Glycoside | α-Glycoside |
| TMS-O-hecogenin | 6 hrs. | 140° C. | xylenes | 33.5% | — |
| TMS-O-11-ketotigogenin | 6 hrs. | 140° C. | xylenes | 43.0% | — |
| TMS-O-diosgenin | 10 hrs. | 140° C. | xylenes | 19% | — |
| TMS-O-cholesterol | 7 hrs. | 140° C. | xylenes | 39% | 0.4% |
| TMS-O-tigogenin | 2 hrs. | 165° C. | decalin | 27% | 0.9% |

EXAMPLE 2

Neat Reaction of β-Cellobiosyl Fluoride Heptaacetate and Trimethylsilyl-O-Tigogenin β-Cellobiosyl fluoride heptaacetate (4.00 g; 6.26 mmol) and trimethylsilyl-O-tigogenin (3.06 g; 6.26 mmol) were dissolved in 10 ml of methylene chloride and then the solvent was evaporated. The white solid mixture was heated to a melt (≈190°–195° C.) under nitrogen. After approximately 10 minutes, the acetofluoro-β-D-cellobiose disappeared by tlc and the melt was cooled to room temperature. The crude product was dissolved in methylene chloride and then analyzed by high-pressure liquid chromatography. Tigogenyl β-O-cellobioside heptaacetate was formed in 36% yield with only 3.0% tigogenyl α-O-cellobioside heptaacetate formation. Acetofluoro-α-D-cellobiose was formed as a reaction by-product.

EXAMPLE 3

Reaction of α-Cellobiosyl Bromide Heptaacetate with Trimethylsilyl-O-Tigogenin

α-Cellobiosyl bromide heptaacetate (0.72 g; 1.03 mmol) and trimethylsilyl-O-tigogenin (0.50 g; 1.02 mmol) were suspended in 3.5 ml of o-xylene under a nitrogen atmosphere. The mixture was slowly heated to 140°–145° C. and then held at that temperature for 6 hours when all the acetobromo-α-D-cellobiose had disappeared. Thin-layer chromatography (ethyl acetate/hexanes eluant 1:1) indicated that no tigogenyl β-O-cellobioside heptaacetate had form. Tigogenin acetate and polar origin materials were the only major products.

EXAMPLE 4

Trimethysilyl-O-Tigogenin

β-Tigogenin (50.0 g, 0.12 mole) and 500 ml of acetonitrile were combined in a one-liter, 3-neck round bottom flask equipped with a mechanical stirrer, distillation head, and thermometer. The mixture was heated to reflux (82° C.) and 100 ml of distillate was removed overhead. The mixture was cooled to 45° C. and then sampled for a Karl Fischer determination (K.F.=0.078% $H_2O$). 1,1,1,3,3,3,-Hexamethyldisilazane (19.0 ml, 0.09 mole) was added and the mixture was heated to 70° C. under nitrogen. After 30 hours at 70° C., thin-layer chromatography (ethyl acetate/hexanes—1:1) showed that the silylation was complete. The mixture was cooled to room temperature and then granulated overnight. The white crystalline solids were filtered and washed with 40 ml of acetonitrile. The product was dried in vacuo at 40° C. for 12 hours to give (25R)-3β-trimethylsiloxy-5-α-spirostan (53.6 g) in 91% overall yield. The product melted at 195°–198° C. and showed good chromatographic and spectral properties.

The title compound could also be prepared in pyridine by using hexamethyldisilazane.

EXAMPLE 5

Trimethylsilyl-O-Hecogenin

To an appropriately equipped flask were added β-hecogenin (95.0 g, 0.22 mole) and 1.43 liters of acetonitrile. The slurry was heated to reflux (82° C.) and 700 ml of distillate was removed overhead. Fresh acetonitrile (500 ml) was added with stirring and then a sample was removed for water analysis (Karl Fischer determination=0.076% $H_2O$). The mixture was cooled to 40° C. and trimethylsilyl chloride (42.0 ml, 0.33 mole) and triethylamine (46.0 ml, 0.50 mole) were added. The mixture was slowly heated to 60° C. due to foaming, and then maintained at 55°–60° C. for 4 hours. Thin-layer chromatography (ethyl acetate/hexanes—1:1) showed only a trace of residual hecogenin so the mixture was cooled to room temperature and granulated overnight. The product was filtered and washed with acetonitrile (2×100 ml). The TMS ether was reslurried in acetonitrile (500 ml), filtered, and then washed with fresh $CH_3CN$ (150 ml). The product was dried (35°–40° C.) at reduced pressure overnight. $^1H$ NMR showed the presence of triethylammonuim hydrochloride in the product; therefore the TMS ether was recrystallized.

Crude TMS-O-hecogenin (50.0 g) was dissolved in 500 ml of methylene chloride to give a light brown solution. Acetonitrile (600 ml) was slowly added to precipitate a white crystalline product. The white solid was granulated for 1 hour, and then filtered and washed with acetonitrile (100 ml). After drying at 45° C. in vacuo overnight, 16.4 grams of product was obtained for a 33% overall yield. (25R)-3β-trimethylsiloxy-5α-spirostan-12-one showed a sharp melting point (m.p.=252°–255° C.) and possessed clean $^1H$ and $^{13}C$ NMR spectral properties.

EXAMPLE 6

Trimethylsilyl-O-11-Ketotigogenin

11-Ketotigogenin (0.93 g, 2.17 mmol) and 10 ml of acetonitrile were added to a 25 ml round bottom flask which was equipped with a mechanical stirrer, thermometer, and reflux condenser. After the apparatus was purged with nitrogen, a sample of the slurry was removed for a Karl Fischer determination (K.F.=0.068% $H_2O$). Triethylamine (0.62 ml. 4.45 mmol) and trimethylsilyl chloride (0.49 ml, 3.86 mmol) were added to the slurry and the mixture was heated to approximately 45° C. After 29 hours at 45° C., thin-layer chromatography (ethyl acetate/hexanes—3:2 eluant)

showed that the reaction was complete. The slurry was cooled to room temperature and then granulated for 1 hour. The product was filtered and then washed with 10 ml of acetonitrile. The white solids were dried in vacuo at 40° C. for 19 hours to give 1.29 grams of crude product. Since $^1$H NMR showed the presence of triethylammonuim hydrochloride, the crude product was reslurried.

The crude TMS ether (1.29 g) was reslurried in 13 ml of absolute methanol for 1 hour. The solids were filtered, washed with fresh methanol (10 ml), and then dried at reduced pressure for 18 hours at 35° C. Trimethylsilyl-O-11-ketotigogenin (0.69 g) was isolated as a white crystalline solid (m.p.=223°–226° C.) in 51% overall yield. The TMS ether was homogeneous by chromatographic assays (tlc) and its $^1$H and $^{13}$C NMR spectra were consistent with its chemical structure, (25R)-3β-trimethylsiloxy-5α-spirostan-11-one.

EXAMPLE 7

Preparation of β-Cellobiosyl Fluoride Heptaacetate

To an appropriately equipped flask, zinc fluoride (2.07 g, 0.02 mole) and 110 ml of acetonitrile were added. The flask was purged and then maintained under a nitrogen atmosphere. The slurry was heated to reflux (82° C.) and then approximately 45 ml of distillate was removed overhead. The slurry was cooled to room temperature and sampled for a Karl Fischer water determination (K.F.=0.034% $H_2O$). α-Cellobiosyl bromide heptaacetate (7.00 g, 0.01 mole) was added and the mixture was heated to 65° C. The slurry was heated for 2.75 hours when thin-layer chromatography (ethyl acetate/hexanes 1:1) showed that the reaction was complete. The reaction was cooled to 25° C., 65 ml of methylene chloride was added, and then the mixture was filtered through Celite. The filtrate was washed with water (50 ml), saturated sodium bicarbonate solution (50 ml), water (50 ml), and finally dried over anhydrous magnesium sulfate (10 g). After filtration, the filtrate was concentrated to about 35–40 ml by an atmospheric distillation and 100 ml of 2B ethanol was added to the warm solution. The solution was again concentrated to about 40 ml and then granulated for 1 hour at 25° C. The solids were filtered and dried at reduced pressure for 16 hours at 45° C. A white solid (4.48 g) was isolated which contained some polar impurities. Crude product was recrystallized from methylene chloride (10 ml) and 2B ethanol (60 ml) as described above (final recrystallization volume=45 ml), and finally recrystallized from hot methanol (40 ml) to give a white crystalline solid (2.30 g, m.p.=163°–166° C.) β-Cellobiosyl fluoride heptaacetate was obtained in a 36% overall yield. High resolution $^1$H and $^{13}$C NMR spectra were in accord with the compound's chemical structure.

The title compound can also be prepared from the reaction of silver fluoride with α-cellobiosyl bromide heptaacetate. To a 2 liter, 3-neck round bottom flask which was equipped with a mechanical stirrer, reflux condenser topped with a nitrogen inlet and wrapped with aluminum foil to exclude light were added α-cellobiosyl bromide heptaacetate (115.0 g, 0.164 mole), silver fluoride (25.0 g, 0.197 mole), and 1.15 liters of acetonitrile. The mixture was stirred for 2.0 hours at 25° C. under nitrogen and then filtered. The brownish filtrate was concentrated to approximately 0.8 liters by an atmospheric distillation. The solution was cooled to ambient temperature, methylene chloride (1.0 liter) was added, and then the resulting solution was washed with water (1.0 liter) and saturated sodium bicarbonate (1.0 liter) solution. After drying the solution over 20 grams of anhydrous magnesium sulfate, the solution was concentrated at reduced pressure to remove the solvent. The crude product was dissolved in ethyl acetate (1.5 liters). The EtOAc solution was passed through a silica gel pad and the product was eluted with additional ethyl acetate (3×0.5 liter). Hexanes (3.0 liter) was added to the combined filtrate and washes to precipitate a white solid. The solids were dried at reduced pressure (45° C.) overnight to give 74.6 grams of product for a 74% overall yield. The acetofluoro-β-D-cellobiose was 99.3% pure by high-pressure liquid chromatographic assay.

The pertinent chemical shifts and coupling constants which were used for assigning the α and β anomeric configurations of acetofluoro-D-cellobioses are reported in Table 2.

TABLE 2

| Anomeric Cellobiosyl Fluoride Heptaacetates - Chemical Shifts and Coupling Constants | | |
|---|---|---|
| Nucleus | β-Fluoride | α-Fluoride |
| Solvent | CDCl$_3$ | CDCl$_3$ |
| H-1 (j$_{1,2}$, J$_{1,F}$) | 5.35 (5.6, 52.6) | 5.65 (2.8, 52.9) |
| C-1 (J$_{C,F}$) | 105.8 (218.8) | 103.6 (229.5) |

We claim:

1. A process for the synthesis of peracyl-1-O-steroidal-β-cellobiosides comprising:

reacting heptaacyl-β-D-cellobiosyl-1-fluoride wherein the acyl is alkanoyl($C_1$–$C_6$), benzoyl or toluoyl and a compound of the formula

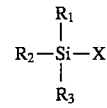

wherein $R_1$, $R_2$, and $R_3$ are each independently alkyl($C_1$–$C_6$), phenyl or phenyl alkyl($C_1$–$C_6$) and X is tigogen-3-O-yl, hecogen-3-O-yl, tigogen-11-keto-3-O-yl or diosgen-3-O-yl in the absence of a metal salt or a Lewis acid under conditions capable of forming said peracyl-1-O-steroidal-β-cellobiosides.

2. The process as recited in claim 1 wherein $R_1$, $R_2$ and $R_3$ are each methyl and the reaction occurs neat or in an aromatic or alkane hydrocarbon solvent.

3. The process as recited in claim 2 wherein X is tigogen-3-O-yl.

4. The process as recited in claim 2 wherein X is hecogen-3-O-yl.

5. The process as recited in claim 2 wherein X is tigogen-11-keto-3-O-yl.

6. The process as recited in claim 2 wherein X is diosgen-3-O-yl.

7. The process as recited in claim 3, 4, 5 or 6 wherein said reaction occurs at about 100° C. to about 220° C. and about 0.5 to about 1.5 equivalents silylated steroid is used.

8. The process as recited in claim 7 wherein the reaction occurs neat.

9. Trimethylsilyl-11-keto-3-β-O-tigogenin.

10. Trimethylsilyl-3-β-O-hecogenin.

11. Trimethylsilyl-3-β-O-tigogenin.

\* \* \* \* \*